(12) United States Patent
de la Torre-Bueno

(10) Patent No.: US 6,445,817 B1
(45) Date of Patent: Sep. 3, 2002

(54) APPARATUS FOR COUNTING COLOR TRANSITIONS AND AREAS IN REAL TIME CAMERA IMAGES

(75) Inventor: Jose de la Torre-Bueno, Encinitas, CA (US)

(73) Assignee: ChromaVision Medical Systems, Inc., San Juan Capistrano, CA (US)

( * ) Notice: Subject to any disclaimer, the term of this patent is extended or adjusted under 35 U.S.C. 154(b) by 0 days.

(21) Appl. No.: 09/615,263

(22) Filed: Jul. 13, 2000

Related U.S. Application Data
(60) Provisional application No. 60/143,824, filed on Jul. 13, 1999.

(51) Int. Cl.⁷ .................................................. G06K 9/00
(52) U.S. Cl. ....................... 382/162; 382/192; 382/194
(58) Field of Search ................................ 382/164, 165, 382/182, 183, 192, 193, 194, 199, 141, 143, 162, 167; 348/86, 87, 91, 125, 126; 702/58; 209/580; 356/418, 425; 714/736; 250/559.47

(56) References Cited

U.S. PATENT DOCUMENTS

| | | | |
|---|---|---|---|
| 4,991,223 A | 2/1991 | Bradley | 382/17 |
| 5,051,816 A * | 9/1991 | Harrison et al. | 714/736 |
| 5,085,325 A | 2/1992 | Jones et al. | |
| 5,087,965 A | 2/1992 | Torre-Bueno | 358/22 |
| 5,706,093 A | 1/1998 | Komiya | |
| 5,799,105 A | 8/1998 | Tao | |
| 5,867,598 A | 2/1999 | de Queiroz | |
| 5,911,003 A | 6/1999 | Sones | |
| 6,097,838 A * | 8/2000 | Klassen et al. | 362/157 |

* cited by examiner

Primary Examiner—Joseph Mancuso
Assistant Examiner—Vikkram Bali
(74) Attorney, Agent, or Firm—Fish & Richardson P.C.

(57) ABSTRACT

A color transition and area counting device for use in a machine vision system may include an input port for inputting a stream of pixels in a frame. The pixels in the frame with particular colors may be counted and stored by associated counters. The frame may be loaded simultaneously into four frame memories. Each frame memory may be read out in a different pattern, for example, horizontally, vertically, diagonally, and cross-diagonally. The number of valid color transitions detected in each of the four read out operations may be added to determine a transition count for the frame. The area count and transition count may be used to flag potentially defective objects examined by the system.

40 Claims, 4 Drawing Sheets

APPARATUS FOR COUNTING COLOR TRANSITIONS AND AREAS IN REAL TIME CAMERA IMAGES

CROSS-REFERENCE TO RELATED APPLICATIONS

This application claims priority to U.S. Provisional Patent Application Serial No. 60/143,824, filed Jul. 13, 1999.

BACKGROUND

Machine vision systems may be used to inspect objects based on their color(s). In industrial applications, such vision systems may inspect the colors of, for example, work pieces, produce, and color-coded pills. Color may be an important indicator of whether a colored component is properly positioned in a work piece, whether produce is ripe or overripe, or whether a particular color-coded pill is in the proper location in its container. Such vision systems may also be used in medical applications to determine the composition of cells, in which different cell components are dyed different colors.

The objects under inspection may be moving on a conveyor belt. Hence, the speed of image processing in the vision system may be an important factor for operational efficiency. The object under inspection may be imaged in a frame of pixels, for example, an array of 680×480 pixels. Each pixel represents the instantaneous value of an optical quality (e.g., color) of the image at a location corresponding to the pixel's position in the frame.

It may be desirable to detect a transition between two colors on an object. For example, a package may contain dark green pills and light green pills in specified locations. If a dark green pill is detected in a location allocated for a light green pill, the package may be considered defective. However, when scanning for dark green pills and light green pills in the package, the sides of the light green pills may include shadows that would cause them to appear dark green to the vision system. This could result in the system erroneously flagging the package as defective. However, by enabling the vision system to identify whether there is a transition between light green and dark green on the same pill, and instructing the system to consider such an occurrence acceptable, such errors may be avoided.

Detecting color transitions may be accomplished by comparing the color of each pixel to that of each of its neighbors. Each pixel in a two dimensional array may have up to eight neighboring pixels. An operation for examining this many pixels may require first storing the image in a frame buffer and then performing a number of search algorithms on the image. Such operations may utilize significant processing resources and may not be performed in real time.

Accordingly, it may be desirable to provide a machine vision system that determines color transitions in a scanned image in real time.

SUMMARY

A color transition counting device according to an embodiment may include a number of transition counting channels. Each channel may include a frame memory and a read out circuit for reading out pixels from the frame memory in a particular pattern. Each channel may also include a transition counter that examines a string of pixels and determines if a valid transition between two colors exists in that string. If so, this transition may be counted and stored in the counter corresponding to that color transition.

The frame memories may be read out at a dot clock rate in horizontal, vertical, diagonal, and cross-diagonal patterns simultaneously by the associated read out circuits. The number of transition detected in each readout operations for that frame may be counted and then added together and this number read out by a host computer.

The device may also include a counting block that includes different counters for different pixel colors of interest. According to an embodiment, the pixels may be one of eight colors. These colors may be keyed colors.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
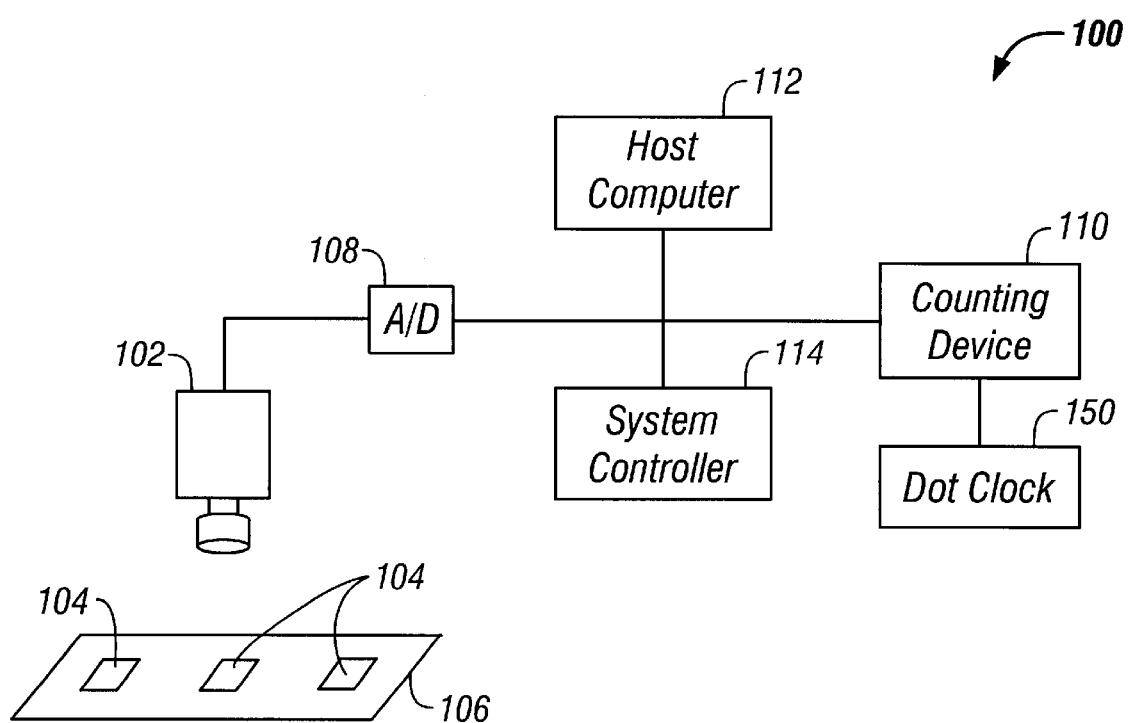
FIG. 1 is a schematic diagram of a machine vision system according to an embodiment.

FIG. 1 illustrates a machine vision system 100 according to an embodiment. A camera 102, which may be analog or digital, scans the images of objects 104 on a base 106, for example, a conveyor belt. The output of the camera 102 may be digitized (if analog) by an analog-to-digital converter (ADC) 108 and input to a color transition and area counting device 110. The counting device 110 accepts color data and outputs a set of counts for each frame. These counts may include the total area of each color and the number of transitions between colors in the image. A host computer 112 may read the counting device output via a device bus with address and data paths 302, 304 (see FIG. 3). The host computer may control a system controller 114 to flag or otherwise act on an inspected object if an error is detected. Such errors may be based on color transitions and color areas determined by the counting device.

According to an embodiment, the vision system 100 operates on eight keyed colors. A keyed color represents a range of raw color values. Pixels in digital images may have one of thousands, even millions, of possible color values (e.g., 16 bit and 24 bit color). Neighboring pixels that appear to have the same color to the naked eye may actually have slightly different color values. For example, in a system using 8 bit color, the two pixels could have values of 00110010 and 00110011. Using this raw color data, a color transition would be considered to exist between these two similar pixels. For many applications, however, such slight differences in color value may not be of interest. Rather, a range of color values representing a color may be of interest when inspecting an object. A keyed color may include a range of color values that fall within upper and lower color value thresholds which are lumped together to represent a single color.

According to an embodiment, the pixels may be transformed upstream of the counting device into one of the eight keyed colors, or none if the pixel has a color value outside of any desired range. Thus, some pixels in the image correspond to one of the eight keyed colors and others may be ignored. Color transitions are considered to occur between adjacent pixels having different keyed colors.

Figure 2:
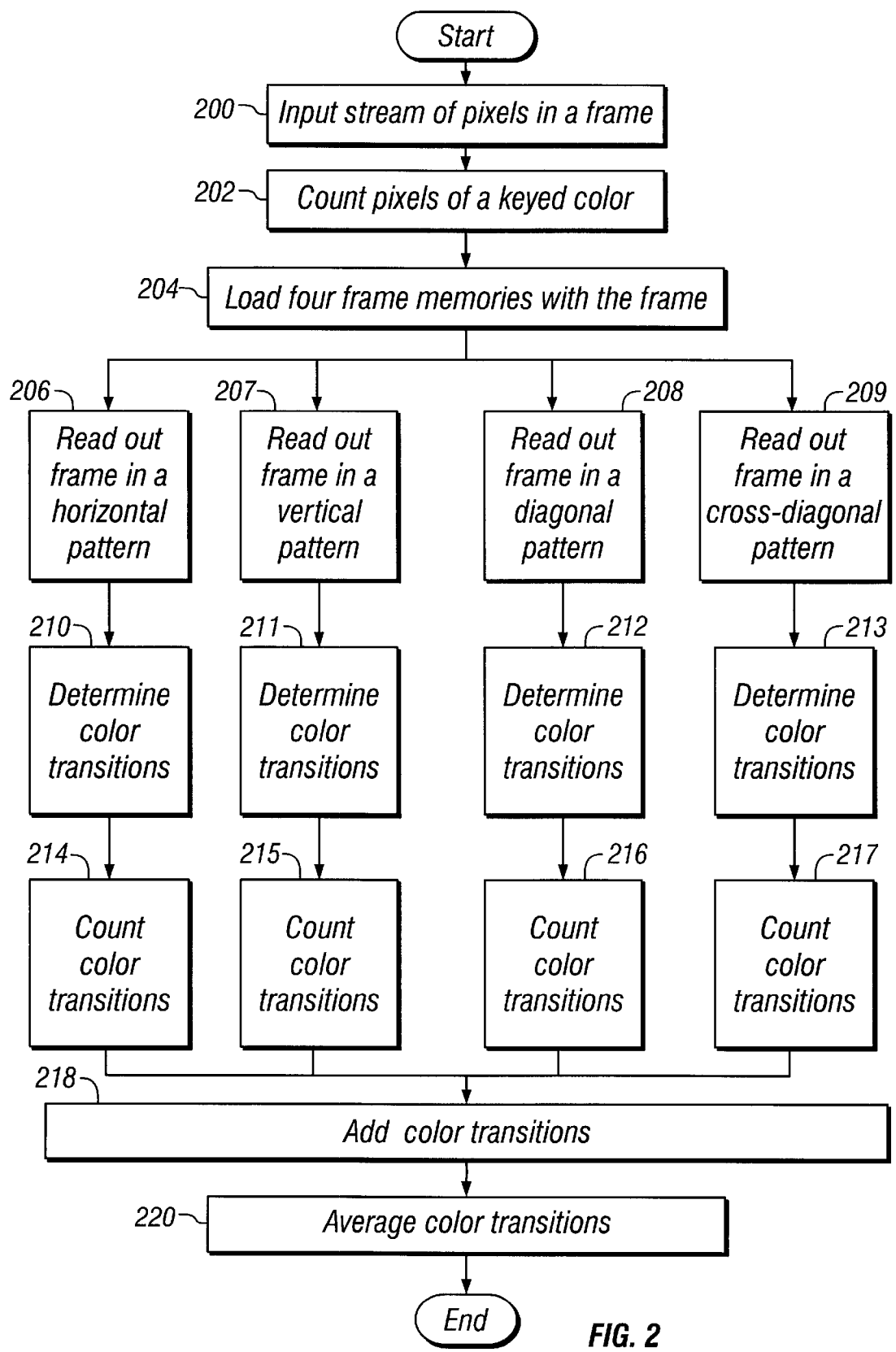
FIG. 2 is a flow diagram illustrating a color area and color transition counting operation according to an embodiment.

FIG. 2 illustrates a color transition and area counting operation according to an embodiment. Pixels in an image are scanned and input to the counting device 110 in state 200. The number of pixels for each color under consideration are counted in state 202. The pixels in the image are also stored simultaneously in each of four frame memories in state 204. These frame memories may be read out in four different patterns including a horizontal pattern, a vertical pattern, a diagonal pattern, and a cross-diagonal pattern in states 206–209. The number of transitions detected in reading out each frame memory in states 210–213 is counted in states 214–217. These counts are added together in state 218 and may be averaged in state 220 to determine a number of color transitions in the image. According to alternate embodiments, this color transition and area counting operation may be implemented in hardware, software, or various combinations of both.

Figure 3A:
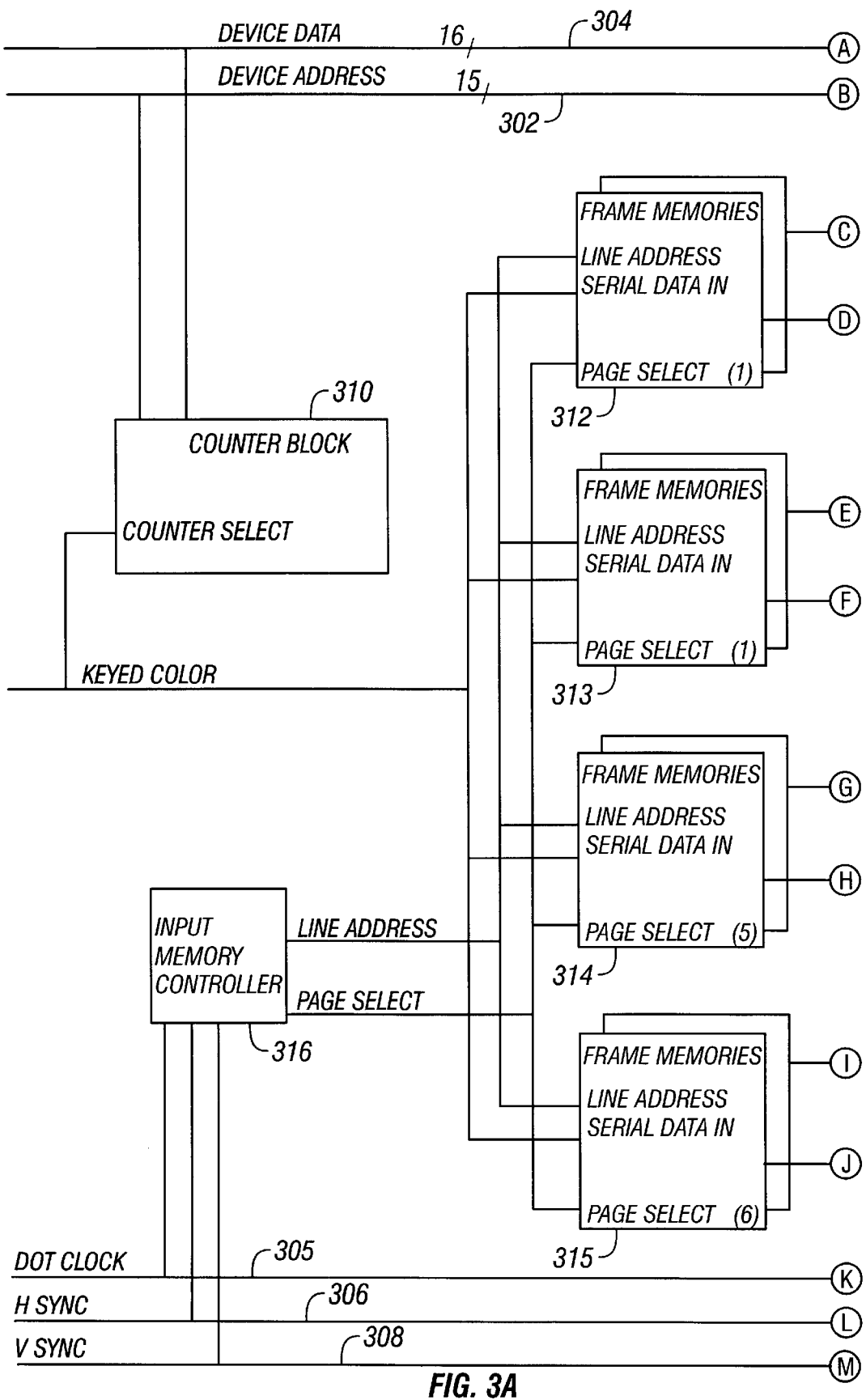
FIG. 3 is a schematic diagram of a color transition and area counting device according to an embodiment.
Figure 3B:
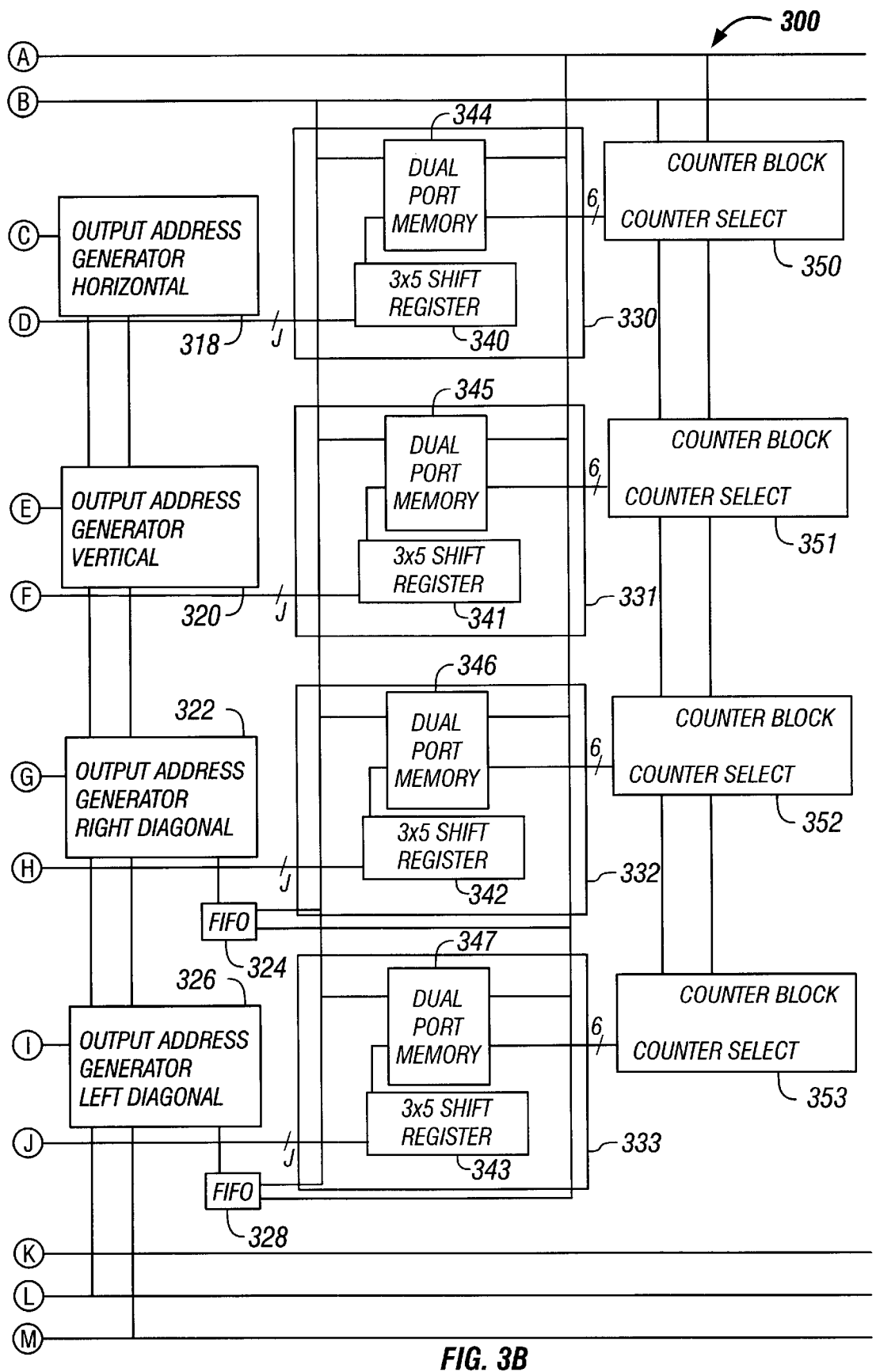

FIG. 3 illustrates a counting device 300 according to an embodiment. The counting device is connected to a dot clock 150 (FIG. 1) and operates at the dot clock rate. Every dot clock signal, three bits are generated by an upstream process indicating which of eight colors the current pixel has. The dot clock signal represents the frequency at which pixels are being scanned in the image. Accordingly, all blocks are clocked by dot clock from line 305. Some blocks also receive horizontal synchronization (hsync) and vertical synchronization (vsync) signals as secondary timing inputs from lines 306 and 308. The host computer 112 may set up various components in the counting device. Each block that may be setup by the host computer or produces results has an address on the device bus.

Areas of each color may be calculated by the first counter block 310. The counter block 310 includes eight counters, one for each color. Every dot clock signal, the counter corresponding to the color of the pixel being read out may be selected and incremented. During vertical blanking (corresponding to the end of a frame) the counters may be read by the host computer 112 and cleared. This provides the total area of the field of view occupied by each color in that frame.

The color data generated upstream may be stored simultaneously in four frame memories 312–315. Each frame memory includes enough video RAM (VRAM) to store two complete frames, a forward frame and a rearward frame, each occupying a different memory location in the frame memory. The counting device may operate in "ping pong" mode, such that as one frame is being read into the frame memories, the previous frame may be analyzed by reading it out of the memory location of the frame memory.

In a scanned video image, an hsync pulse may signal the end of a row of pixels, and the vsync pulse may signal the end of a frame. An input memory controller 316 may generate a page select signal that switches between HIGH and LOW values each vsync signal to select one of the stored frames. The input memory controller 316 performs an input process in which a forward frame of each frame memory is input to the frame memory on the HIGH phase and a rearward frame input on the LOW phase. The input controller may also perform an output process in which the rearward frame of each frame memory is output to the frame memory on the HIGH phase and a forward frame output on the LOW phase. The input memory controller may generate line addresses and other signals utilized by the VRAMs. The line addresses may be determined from the dot clock, hsync, and vsync signals.

Transitions in color along edges or perimeters of a scanned object may be calculated by circuitry downstream of the frame memories. Edges may be found by streaming the data out of the frame memories in four different patterns: horizontal; vertical; diagonal; and cross-diagonal. The cross-diagonal pattern is a diagonal pattern perpendicular to the other diagonal pattern. These four frame memories and downstream circuitry in the counting device form four directional channels.

An output address generator 318 for the horizontal pattern produces a standard raster scan, i.e., the data comes out of the frame memory in the same order it went in. This address generator may include two counters, one that counts dot clock pulses and is cleared by an hsync pulse, which indicates the end of a row, and another that counts the hsync pulses and is cleared by a vsync pulse, which indicates the end of a frame.

An output address generator 320 for the vertical pattern produces a read out by columns rather than rows. If the frame memories are square, the same circuit may be used for the horizontal and vertical patterns by swapping the row and column addresses between frame memories 312 and 313.

An output address generator 322 produces a sequence of addresses which scan the frame memory in a diagonal pattern. The output address generator may include a first-in first-out (FIFO) register 324 that may be loaded by the host computer at setup with the start X, Y coordinates and length of each diagonal segment in the scanning pattern and the direction X and Y are to be incremented or decremented along the diagonal segment. The output address generator may also include a counter which may be loaded with the length of the diagonal segment from the FIFO and which counts down the length of the line segment. When this counter counts to zero, a start point and length for a new diagonal segment may be loaded from the FIFO. At vsync the FIFO may be reset. According to this embodiment, there is no need to reload the FIFO once it is set up since each frame is analyzed in the same pattern.

An output address generator 324 produces a sequence of addresses which scan the frame memory in a cross-diagonal pattern, that is, a diagonal pattern perpendicular to that generated by the output address generator 322 described above. This output address generator 324 may have a structure similar to that of output address generator 322, the FIFO 328 being loaded with another set of instructions corresponding to the cross-diagonal pattern. If the frame memories are square the same circuit may be used for the horizontal and vertical patterns by swapping the row and column addresses between frame memories 314 and 315.

The next two sets of blocks count color transitions. Because the frame is scanned in four different directions, the effect of orientations may be reduced. For instance, a horizontal long thin object may have few transitions when scanned horizontally, but it would have more transitions when scanned vertically. By combining the transition counts from four directions of scan, a substantially orientation independent edge count may be produced.

Noise may be encountered at a transitional edge between two colors. For example, given an edge between two colors 4 and 5, the pattern along a given scan direction may not be a discrete pattern like 444555, but rather something like 445455 or 442555, where 2 is some other color. If every transition between two colors is counted, such noise may obscure the actual border of the color regions and give spuriously high counts.

According to an embodiment, four transition determining circuits 330–333 are provided, one for each directional channel. Each of the transition determining circuits examines a running pattern six pixels long and decides whether the pattern should be considered a transition. Each transition determining circuit includes three parallel shift registers 340–343 six bits deep with parallel output. Each shift register receives three bits each clock cycle and at any moment is outputting eighteen bits representing the colors received for the last six pixels. Each transition determining circuit includes a dual port memory 344–347 that may be loaded by the host computer at setup with a set of rules defining which bit patterns are to be considered true transitions between which colors. For example, both 444555 and 445455 may be considered true for a 4 to 5 transition. If one of these patterns is detected, a counter clock pulse is generated indicating that a transition occurred, and a counter address is generated corresponding to a counter in a corresponding one of the counter blocks 350–353 which is accumulating color 4 to 5 and 5 to 4 transitions. This counter is then incremented. In the same example, the pattern 454545 might be considered noise, and if detected, a transition would not be counted and none of the counters in the counter block incremented.

According to an embodiment utilizing eight colors, twenty eight transitions are possible since there is no transition between a color and itself, and transitions back and forth between a pair of colors are counted as the same type of transition since the direction is an accident of orientation. Accordingly, each of the counter blocks 350–353 include twenty eight counters. During vertical blanking the host may unload these counters and clear them. By adding or averaging the counters representing the same color transition determined from each scan direction, the host computer can arrive at a count of color transitions largely independent of orientation. For many recognition tasks, the color area information together with the color transition information may provide enough information to make useful discriminations.

According to alternate embodiments, the number of colors processed, the size of the frame memories, and the depth of the shift registers may be changed to suit different tasks. Increasing the number of colors may entail increasing the size of the shift registers, the size of the dual port memories, the number of counters in the counter banks, and the depth of the frame stores. Increasing the depth of the shift registers may allow longer transition patterns to be simplified but may increase the size requirements of the dual ports.

A machine vision system according to an embodiment may be used for a variety of industrial and medical applications including, for example, inspecting colored components in a work piece, produce, color-coded pills, textiles, and stained cells.

For objects inspected for specific colors in predetermined locations in the object, the image may be masked and only pixels in the masked regions examined for color transitions and color area counts. Different masked regions may be examined for different color transitions and color area counts.

Since the object image may be analyzed in real time at dot clock rates, a vision system according to an embodiment may be well suited to assembly line-type applications. The color transition and area count may be used as a preliminary scan to determine areas including potential defects based on color counts. These areas may then be further examined using more thorough color analysis operations to determine if a defect in fact exists.

A number of embodiments of the invention have been described. Nevertheless, it will be understood that various modifications may be made without departing from the spirit and scope of the invention. Accordingly, other embodiments are within the scope of the following claims.

What is claimed is:

1. Apparatus comprising:
    a plurality of transition counting channels, each transition counting channel including:
    a frame memory to store a frame including a plurality of pixels, each pixel having a color value, wherein the frame memories in the plurality of transition counting channels all contain the same frame;
    a read out circuit to read out the pixels in the frame memory in a particular pattern, each of said read out circuits adapted to read out the pixels in said same frame in a different pattern, at least one pattern being other than a horizontal or vertical pattern; and
    a transition counter to count and store a number of transitions between two colors detected in a string comprising a plurality of said pixels.

2. The apparatus of claim 1, wherein the pixel color values comprise keyed colors.

3. The apparatus of claim 1, wherein the pixels may have one of eight keyed colors.

4. The apparatus of claim 1, further comprising:
    an input port to receive a stream of pixels; and
    a plurality of counters connected to the input port, each counter adapted to count pixels having a particular color value.

5. The apparatus of claim 1, wherein each transition counter comprises a plurality of counters, each counter adapted to count a transition between two different color values.

6. The apparatus of claim 1, further comprising a memory connected to the transition counter, said memory including instructions to identify pixel strings corresponding to a valid color transition.

7. The apparatus of claim 1, wherein each frame counter is adapted to store two frames.

8. The apparatus of claim 1, wherein the transition counters operate at a dot clock rate.

9. The apparatus of claim 1, wherein one of said read out circuits reads out the associated frame memory in a horizontal pattern.

10. The apparatus of claim 1, wherein one of said read out circuits reads out the associated frame memory in a vertical pattern.

11. The apparatus of claim 1, wherein one of said read out circuits reads out the associated frame memory in a diagonal pattern.

12. The apparatus of claim 11, wherein one of said read out circuits reads out the associated frame memory in a diagonal pattern perpendicular to the diagonal pattern of said other read out circuit.

13. The apparatus of claim 1, wherein the different patterns comprise a horizontal pattern, a vertical pattern, a first diagonal pattern, and a second diagonal pattern transverse to the first diagonal pattern.

14. The apparatus of claim 1, further comprising an adding unit operative to add the number of transitions stored in each of the transitions counters in the plurality of transition counting channels.

15. The apparatus of claim 1, further comprising an averaging unit operative to average the number of transitions stored in each of the transitions counters in the plurality of transition counting channels.

16. Apparatus comprising:
a plurality of transition counting channels, each transition counting channel including:
a frame memory to store a frame including a plurality of pixels, each pixel having a color value;
a read out circuit to read out the pixels in the frame memory in a particular pattern, each of said read out circuits adapted to read out the pixels in a different pattern; and
a transition counter to count and store a number of transitions between two colors detected in a string comprising a plurality of said pixels, wherein the pixels may have one of eight keyed colors, and wherein each transition counter includes twenty-eight counters.

17. Apparatus comprising:
a plurality of transition counting channels, each transition counting channel including:
a frame memory to store a frame including a plurality of pixels, each pixel having a color value;
a read out circuit to read out the pixels in the frame memory in a particular pattern, each of said read out circuits adapted to read out the pixels in a different pattern, at least one pattern being other than a horizontal or vertical pattern;
a transition counter to count and store a number of transitions between two colors detected in a string comprising a plurality of said pixels; and
a memory for storing the start point coordinates and a length of each of a plurality of diagonal segments, and a counter for counting out the length of each diagonal segment.

18. A system comprising:
a camera to image an object;
a digitizer connected to the camera to digitize the image into a frame comprising a plurality of pixels, each pixel having a color value;
a color counter comprising:
an input port to receive a stream of pixels in the frame from the digitizer;
a dot clock to produce a clocking signal at a rate corresponding to a rate at which pixels are input to counter; and
a plurality of transition counting channels, each channel including
a frame memory to store the frame, wherein the frame memories in the plurality of transition counting channels all contain the same frame,
an output address generator to read out the pixels in the frame memory in a particular pattern, each of said output address generators adapted to read out the pixels in said same frame in a different pattern, at least one pattern being other than a horizontal or vertical pattern, and
a transition counter to count and store a number of transitions between two colors detected in a string comprising a plurality of said pixels at the dot clock rate.

19. The system of claim 18, wherein the color values comprise keyed colors.

20. The system of claim 18, wherein the pixels may have one of eight keyed colors.

21. The system of claim 18, further comprising:
an input port to receive a stream of pixels; and
a plurality of counters connected to the input port, each counter adapted to count a number of pixels having a particular color value.

22. The system of claim 18, further comprising:
a host machine to read out the number of transitions from each of the transition counters at the end of a frame; and
a system controller to flag an object in response to the number of transitions read out from the transition counters.

23. A method comprising:
storing a frame in a plurality of frame memories, said frame comprising a plurality of pixels having color values; wherein said plurality of frame memories all contain the same frame
outputting the pixels from said same frame in each frame memory in a different pattern, at least one pattern being other than a horizontal or vertical pattern;
determining a number of transitions between two colors in a string of pixels for each frame memory; and
adding the number of transitions between the two colors.

24. The method of claim 23, wherein the color values comprise keyed colors.

25. The method of claim 23, further comprising averaging the number of transitions counted between the plurality of frame memories.

26. The method of claim 23, further comprising:
inputting a stream of pixels to the frame memories;
counting and storing a number of pixels having a particular color value.

27. The method of claim 23, wherein the transitions are counted at a dot clock rate.

28. The method of claim 23, wherein pixels are output from a frame memory in a horizontal pattern.

29. The method of claim 23, wherein pixels are output from a frame memory in a vertical pattern.

30. The method of claim 23, wherein pixels are output from a frame memory in a diagonal pattern.

31. The method of claim 23, wherein pixels are output from a frame memory in a diagonal pattern perpendicular to the pattern of said other diagonal pattern.

32. An apparatus including instructions residing on a machine-readable medium for use in a vision system for counting color transitions in an image, the instructions causing the machine to:
store a frame in a plurality of frame memories, said frame comprising a plurality of pixels having color values; wherein said plurality of frame memories all contain the same frame
output the pixels from said same in each frame memory in a different pattern, at least one pattern being other than a horizontal or vertical pattern;
determine a number of transitions between two colors in a string of pixels for each frame memory; and
add the number of transitions between the two colors.

33. The apparatus of claim 32, wherein the color values comprise keyed colors.

34. The apparatus of claim 32, further comprising instruction that cause the machine to average the number of transitions counted between the plurality of frame memories.

35. The apparatus of claim 32, further comprising instructions that cause the machine to:
input a stream of pixels to the frame memories;
count and store a number of pixels having a particular color value.

36. The apparatus of claim 32, wherein the instructions cause the machine to count the transitions at a dot clock rate.

37. The apparatus of claim 32, wherein the instructions cause the machine to output pixels from a frame memory in a horizontal pattern.

38. The apparatus of claim 32, wherein the instructions cause the machine to output pixels from a frame memory in a vertical pattern.

39. The apparatus of claim 32, wherein the instructions cause the machine to output pixels from a frame memory in a diagonal pattern.

40. The apparatus of claim 32, wherein the instructions cause the machine to output pixels from a frame memory in a diagonal pattern perpendicular to the pattern of said other diagonal pattern.

* * * * *